US00PP08507P

United States Patent [19]

Meilland

[11] Patent Number: Plant 8,507

[45] Date of Patent: Dec. 21, 1993

[54] HYBRID TEA ROSE PLANT NAMED 'MEISUNTEF'

[75] Inventor: Alain A. Meilland, Antibes, France

[73] Assignee: The Conard-Pyle Company, West Grove, Pa.

[21] Appl. No.: 983,322

[22] Filed: Nov. 30, 1992

[51] Int. Cl.[5] ..... A01H 5/00

[52] U.S. Cl. ..... Plt./20

[58] Field of Search ..... Plt./20, 21

*Primary Examiner*—Howard J. Locker

*Attorney, Agent, or Firm*—Burns, Doane, Swecker & Mathis

[57] ABSTRACT

A new and distinct variety of hybrid tea rose plant is provided which forms attractive velvety fully double red blossoms on very long stems. The blossoms are cardinal red suffused with vermilion red. The buds are very large. The blossoms are long lasting when cut and placed in a vase and their cleaning ability is good. The plant exhibits an upright growth habit, vigorous vegetation, and is particularly suited for cut flower production under greenhouse growing conditions. Also, the new variety exhibits excellent disease resistance.

1 Drawing Sheet

SUMMARY OF THE INVENTION

The new variety of hybrid tea rose plant was created by artificial pollination wherein two parents were crossed with previously had been studied in the hope that they would contribute the desired characteristics. The female parent (i.e., the seed parent) of the new variety was the MEIRED variety (U.S. Plant Pat. No. 3,452) and the male parent (i.e., the pollen parent) was the ROYALTY variety (U.S. Plant Pat. No. 4,057). The MEIRED variety sometimes is known as the VISA variety. The parentage of the new variety can be summarized as follows:

MEIRED×ROYALTY.

The seeds resulting from the above pollination were sown and 11 small plants were obtained which were physically and biologically different from each other. Selective study resulted in the identification of a single plant of the new variety.

It was found that the new variety of hybrid tea rose plant of the present invention possesses the following combination of characteristics:

(a) forms large dark red buds,
(b) forms on very long stems attractive long lasting fully double velvety flowers which are a very stable Cardinal Red suffused with Vermillion Red,
(c) exhibits an upright growth habit,
(d) exhibits vigorous vegetation,
(e) is particularly suited for cut flower production under greenhouse growing conditions, and
(f) exhibits excellent disease resistance.

The cleaning ability of the blooms after flowering is excellent.

The new variety well meets the needs of the horticultural industry for a number of uses and is particularly well suited for use during the formation of cut flowers.

The new variety has been found to undergo asexual propagation in France by a number of routes, including budding, grafting, cuttage, etc. The characteristics of the new variety have been found to be strictly transmissible by such asexual propagation from one generation to another.

The new variety has been named the MEISUNTEF variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were one year of age and were observed during February while budded on *Rosa indica* understock and growing in greenhouses at Cap d'Antibes, France.

FIG. 1—illustrates a specimen of young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower during the course of opening;

FIG. 6—illustrates a specimen of an open flower - plan view - obverse;

FIG. 7—illustrates a specimen of an open flower - plan view - reverse;

FIG. 8—illustrates a specimen of a fully open flower - plan view - obverse;

FIG. 9—illustrates a specimen of a fully open flower - plan view - reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets - plan view - upper surface;

FIG. 15—illustrates specimen of a leaf with five leaflets - plan view - under surface; and FIG. 16—illustrates a specimen of a leaf with seven leaflets - plan view - upper surface.

DETAILED DESCRIPTION

Figures 1, 2, 3, 4, 5, 6, 7, 8, 9, 10, 11, 14, 15, 16:
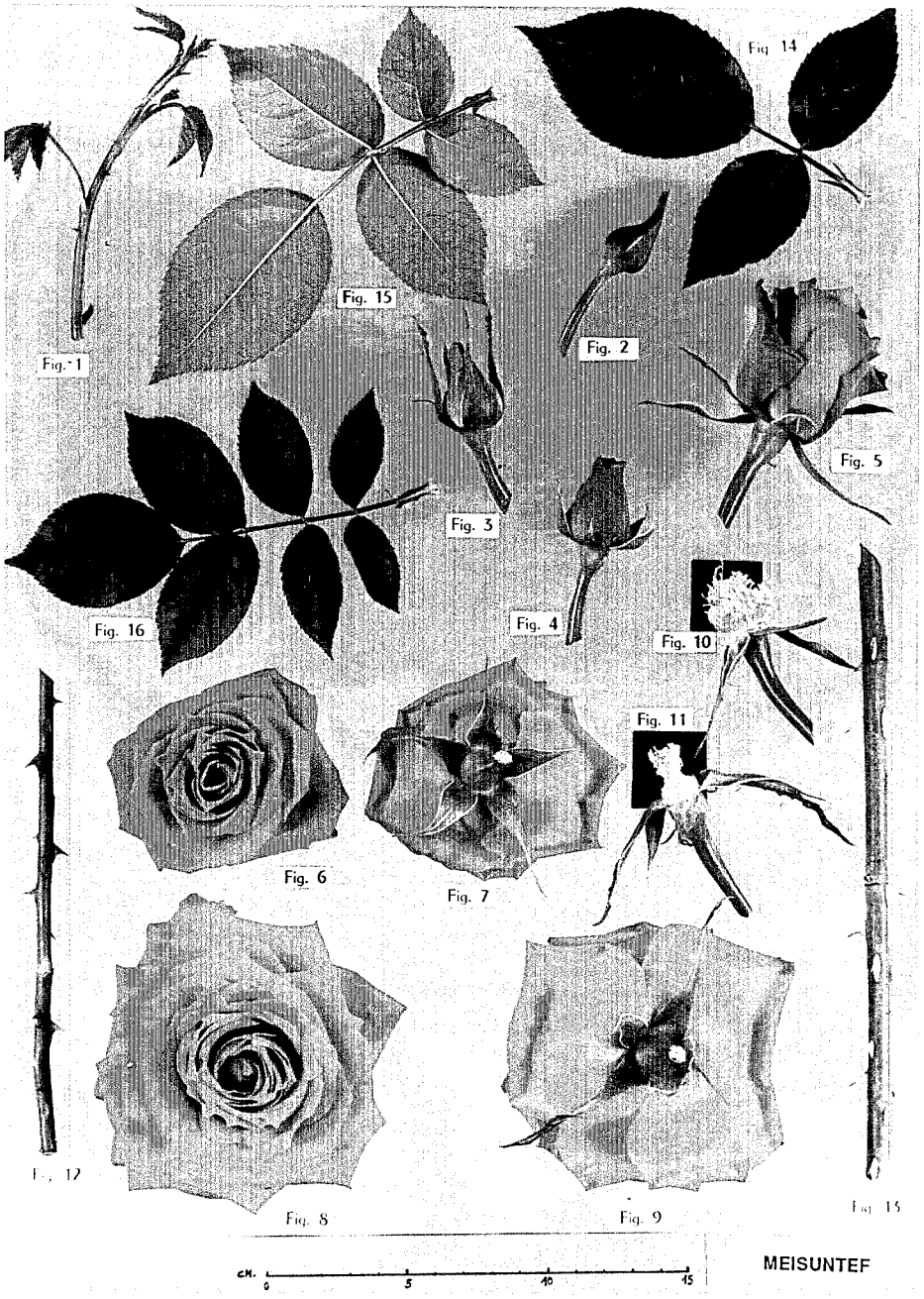

The chart used in the identification of the colors is that of The Royal Horticultural Society (R.H.S. Colour Chart). The description is based on the observation of one year old plants made during February while budded on Rosa indica understock and growing in greenhouses at Cap d'Antibes, France. The coloration in common terms precedes reference to the chart.

Class: Hybrid tea.

Plant:

*Height.*—When plants are cut to a height of 85 cm. flowering stems commonly are produced having a length of approximately 70 to 90 cm. When grown in fields at Wasco, Calif., U.S.A., the plants commonly attain a height of approximately 140 to 160 cm. at the end of one growing season.

*Habit.*—Upright.

Branches:

*Color.*—Young stems: light green, Green Group 143B, more or less widely suffused with reddish coloration. Adult wood: medium green, Green Group 137B.

*Thorns.*—Size: small. Quantity: average. Color: pinkish on young stems and greenish changing to tan on mature wood.

Leaves:

*Stipules.*—Adnate, pectinate and linear.

*Petioles.*—Upper surface: striped reddish brown on young foliage and medium green on adult foliage with more or less grandular edges. Under surface: light green, and bears numerous prickles.

*Leaflets.*—Number: 3, 5 (most often), and 7. Shape: spear-shaped. Serration: regular. Texture: consistent. General appearance: dense and semi-matte foliage. Color (young foliage): upper surface: dark green, Green Group 143A. under surface: medium green, Green Group 143B, and widely suffused with reddish coloration. Color (adult foliage): upper surface: dark green, Green Group 137A. under surface: grayish green, Greyed-Green Group 191A.

Inflorescence:

*Number of flowers.*—Usually a single bloom per stem.

*Peduncle.*—Medium green and more or less suffused with reddish coloration. The length is approximately 13 to 15 cm. on average.

Sepals.—Upper surface: tomentose and greenish. Under surface: medium green in coloration, the outer sepals are more or less glandular and have slightly appendiculated edges.

*Buds.*—Shape: conical. Length: approximately 4 cm. on average. Size: large. Color when opening: upper surface: velvety Cardinal Red, Red Group 53A. under surface: velvety Cardinal Red, Red Group 53A.

*Flower.*—Shape: somewhat cup-like and fully double. Diameter: approximately 13 cm. on average. Color (when opening begins): upper surface: velvety medium Cardinal Red, Red Group 53B, and more or less suffused with Vermilion Red, Red Group 44 B. Under surface: velvety medium Cardinal Red, Red Group 53B, and more or less suffused with Vermilion Red, Red Group 44B. Color (when blooming): upper surface: velvety medium Cardinal Red, Red Group 53B, and more or less suffused with Vermilion Red, Red Group 44B. under surface: velvety medium Cardinal Red, Red Group 53B, and more or less suffused with Vermilion Red, Red Group 44B. Color (at end of blooming): upper surface: velvety medium Cardinal Red, Red Group 53B, and more or less suffused with Vermilion Red, Red Group 44B. under surface: velvety medium Cardinal Red, Red Group 53B, and more or less suffused with Vermilion Red, Red Group 44B. Fragrance: none. Lasting quality: long lasting when cut and placed in a vase. Petal number: approximately 40 to 50 on average. Texture: consistent. Petal drop: good. Petal configuration: rounded. Stamen number: approximately 119 on average. Anthers: long, yellowish in coloration with fuchsia centers, and located well below the stigmas. Filaments: fuschia in coloration, with a yellowish base, and of irregular heights. Pistils: approximately 135 on average. Stigmas: straw-like. Styles: light fuchsia in coloration, long, and tomentose near base. Receptacle: smooth, medium green and funnel-shaped.

Development:

*Vegetation.*—Vigorous.

*Blooming.*—Normal.

*Aptitude to be forced.*—Good.

*Resistance to diseases.*—Very good.

I claim:

1. A new and distinct variety of the hybrid tea rose plant characterized by the following combination of characteristics:

(a) forms large dark red buds,
(b) forms on very long stems attractive long lasting fully double velvety flowers which are a very stable cardinal red suffused with vermilion red,
(c) exhibits an upright growth habit,
(d) exhibits vigorous vegetation,
(e) is particularly suited for cut flower production under greenhouse growing conditions, and
(f) exhibits excellent disease resistance;

substantially as herein shown and described.

* * * * *

CM.
0
5
10
15
MEISUNTEF